United States Patent
Lorenzetto

(10) Patent No.: US 12,042,311 B2
(45) Date of Patent: Jul. 23, 2024

(54) RADIOLOGICAL FILTER

(71) Applicant: Epica International, Inc., San Clemente, CA (US)

(72) Inventor: Cosimo Lorenzetto, Impruneta (IT)

(73) Assignee: EPICA INTERNATIONAL, INC., San Clemente, CA (US)

( * ) Notice: Subject to any disclaimer, the term of this patent is extended or adjusted under 35 U.S.C. 154(b) by 409 days.

(21) Appl. No.: 17/429,318

(22) PCT Filed: Jan. 31, 2020

(86) PCT No.: PCT/IB2020/050799
§ 371 (c)(1),
(2) Date: Aug. 6, 2021

(87) PCT Pub. No.: WO2020/161583
PCT Pub. Date: Aug. 13, 2020

(65) Prior Publication Data
US 2022/0104780 A1  Apr. 7, 2022

(30) Foreign Application Priority Data
Feb. 6, 2019 (IT) .......................... 102019000001743

(51) Int. Cl.
*A61B 6/03* (2006.01)
*G06T 7/00* (2017.01)
*G21K 1/10* (2006.01)

(52) U.S. Cl.
CPC ............ *A61B 6/032* (2013.01); *G06T 7/0012* (2013.01); *G21K 1/10* (2013.01); *G06T 2207/10081* (2013.01)

(58) Field of Classification Search
None
See application file for complete search history.

(56) References Cited

U.S. PATENT DOCUMENTS

| 4,181,858 | A | 1/1980 | Moore | |
|---|---|---|---|---|
| 6,645,196 | B1 * | 11/2003 | Nixon | A61B 34/37 606/1 |
| 7,082,189 | B2 * | 7/2006 | Yahata | A61B 6/06 378/158 |
| 7,283,604 | B2 * | 10/2007 | De Man | A61B 6/482 378/207 |
| 2005/0013411 | A1 * | 1/2005 | Yahata | G21K 1/04 378/156 |

(Continued)

OTHER PUBLICATIONS

International Search Report and Written Opinion for International Application No. PCT/IB2020/050799 dated Apr. 2, 2020.

*Primary Examiner* — Anand P Bhatnagar
(74) *Attorney, Agent, or Firm* — STEPTOE LLP; Carl B. Wischhusen

(57) ABSTRACT

A radiological filter includes a first working surface and a second working surface. The second working surface is placed opposite the first working surface to enable an x-ray beam to pass through the filter via the first and second working surfaces. The first working surface comprises first and second sectors, the first sector defining a first portion, which is substantially flat, and the second sector defining a second portion, which is substantially curved and complementary to the first portion.

14 Claims, 3 Drawing Sheets

(56) References Cited

U.S. PATENT DOCUMENTS

| | | | |
|---|---|---|---|
| 2005/0089146 A1* | 4/2005 | Toth | A61B 6/032 378/158 |
| 2006/0109950 A1* | 5/2006 | Arenson | A61B 6/583 378/4 |
| 2007/0116170 A1* | 5/2007 | De Man | G06T 5/20 378/4 |
| 2008/0013689 A1* | 1/2008 | Toth | G21K 1/10 378/158 |
| 2010/0246775 A1* | 9/2010 | Yuan | G21K 1/10 378/158 |
| 2015/0036792 A1* | 2/2015 | Yi | A61B 6/542 378/4 |
| 2017/0273645 A1* | 9/2017 | Raupach | G21K 1/025 |

* cited by examiner

RADIOLOGICAL FILTER

CROSS-REFERENCE TO RELATED APPLICATIONS

This application is a National Stage Filing based on and claiming priority from International Application No. PCT/IB2020/050799, filed Jan. 31, 2020, which claims priority from Italian Patent Application No. 102019000001743, filed Feb. 6, 2019, each of which is incorporated by reference in its entirety.

FIELD OF THE INVENTION

The present invention relates to a radiological filter. In particular, the present invention relates to a radiological imaging device equipped with a radiological filter that can be used in human and/or animal medicine.

BACKGROUND

As known, the wholly animal and/or human use radiological imaging devices comprise an x-ray emitter and a detector that are available on the opposite side of the patient, and a patient support. The x-ray emitter includes an x-ray source designed to generate and then emit an x-ray beam, at least one collimator defining the shape of the beam, and a filter for removing the low-energy component that is not useful for creating the image and is harmful to the patient. The collimator is usually divided into two parts, i.e., a fixed primary collimator, placed upstream of the filter, having the shape of a truncated cone and defining the maximum angular dispersion of the beam, and a secondary collimator, placed downstream of the filter, consisting of two pairs of variable opening blocks defining the size of the treatment field. In some cases, the radiological devices may include a portal defining an analysis zone wherein the portion to be analysed is inserted, supporting, and commanding the emitter and detector to rotate.

The described prior art comprises some significant drawbacks. In particular, the filters on the market today are specific to only one type of radiological acquisition; therefore, multifunctional radiological imaging devices, i.e., those able to perform two or more fluoroscopies, radiographs, or tomographies, require one or more filters for each type of acquisition. For this reason, they must be equipped with an exchange member that varies the filter hit by the X-ray beam according to the acquisition to be carried out. This solution, in addition to increasing the costs and size of the devices, makes it impossible to have an adequate number of filters. For the reasons explained above, multifunctional radiological imaging devices are expensive and complex to implement and, therefore, not very widespread today.

SUMMARY

Under these circumstances, the technical purpose of one embodiment of the present invention is to devise a radiological filter that is able to substantially overcome at least some of the drawbacks mentioned above. Within the sphere of this technical purpose, one important purpose of the invention is to obtain a radiological filter that can be used for more than one type of radiological acquisition. In particular, an important purpose of one embodiment of the invention is to provide a multifunctional radiological device with reduced costs and a reduced size.

BRIEF DESCRIPTION OF THE DRAWINGS

The various embodiments of the invention are described in the following detailed description, with reference to the accompanying drawings, wherein.

DETAILED DESCRIPTION

Figure 1:
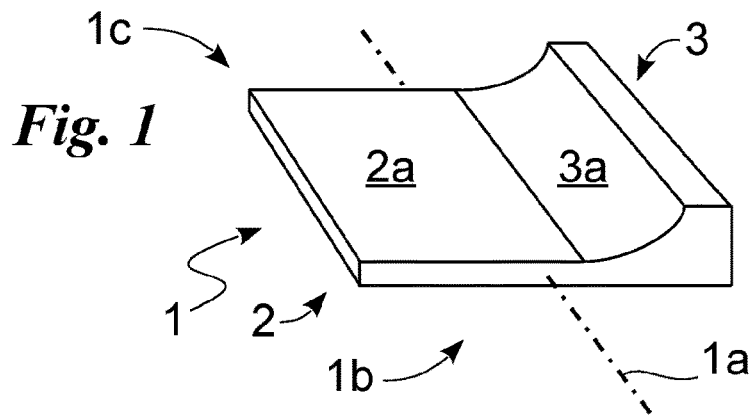
FIG. 1 shows, in scale, a radiological filter according to an embodiment of the present invention.

In this document, the measurements, values, shapes, and geometric references (such as perpendicularity and parallelism), when associated with words like "almost" or other, similar terms such as "approximately" or "substantially," are to be understood to the extent of measurement errors or inaccuracies owing to production and/or manufacturing errors and, above all, to the extent of a slight divergence from the value, measurement, shape, or geometric reference with which it is associated. For example, if such terms are associated with a value, they preferably indicate a divergence of not more than 10% of the same value.

Furthermore, when used, terms such as "first," "second," "higher," "lower," "main," and "secondary" do not necessarily identify an order, relationship priority, or relative position, but they can simply be used to distinguish more clearly between different components.

The measurements and data provided in this text are to be considered as performed in ICAO International Standard Atmosphere (ISO 2533), unless otherwise indicated.

Unless otherwise indicated, as evidenced by the discussions below, it should be understood that terms such as "processing," "computer," "computing," "evaluation," or the like, refer to the action and/or processes of a computer or similar electronic calculation device, which handles and/or processes data represented as physical, such as electronic sizes of logs of a computer system and/or their memories, other data similarly represented as physical quantities inside computer systems, logs or other information storage, transmission or display devices.

With reference to the figures, reference numeral 1 globally denotes the radiological filter according to an embodiment of the invention. Radiological filter 1 may be part of an x-ray emitter 10 and, in particular, of an x-ray beam 10a. Preferably, it can be part of a radiological imaging device 100 designed to carry out radiological imaging of at least part of a patient 1d. Preferably, radiological imaging device 100 is multifunctional and, to be precise, able to carry out a tomography and at least one of either fluoroscopy or radiography. In detail, imaging device 100 is multifunctional and capable of performing tomography, fluoroscopy, and radiography.

It should be noted that patient 1d can be either human or animal.

X-ray beam 10a defines an emission axis 10b that is barycentric to the beam. It can be conical. Radiological filter 1 defines a longitudinal axis 1a, a first working surface 1b, and a second working surface 1c opposite first working surface 1b with respect to the same radiological filter 1.

Working surfaces 1b and 1c define the surfaces for which x-ray beam 10a passes through the radiological filter and then through which x-ray beam 10a enters and exits radiological filter 1. X-ray beam 10a preferably enters radiological filter 1 through second working surface 1c and exits radiological filter 1 through first working surface 1b. First working surface 1b is on the opposite side from second working surface 1c in relation to the same radiological filter 1.

Radiological filter 1 comprises a first sector 2 defining a first portion 2a of first working surface 1b, which is substantially flat, and a second sector 3 defining a second portion 3a of first working surface 1b, the profile of which is substantially curved, extending along longitudinal axis 1a. Sectors 2 and 3 extend substantially parallel to longitudinal axis 1a. As a result, radiological filter 1 has an L-like profile.

In detail, second portion 3a has the profile of a semi-parabola extending along longitudinal axis 1a. The semi-parabola has a symmetry axis parallel to first portion 2a. The semi-parabola has an external focus and, more specifically, on the opposite side of radiological filter 1. Second portion 3a is complementary to first portion 2a in relation to first working surface 1b and, therefore, totally defined by portions 2a and 3a.

Second working surface 1c is substantially flat and, more specifically, parallel to first portion 2a. First sector 2 defines an additional first portion of second working surface 1c. The additional first portion can be substantially flat. Alternatively, it may have a substantially curved profile extending along longitudinal axis 1a.

Second sector 3 defines an additional second portion 3a of the second working surface 1c that is substantially flat. The additional second portion can be substantially flat. Alternatively, it may have a substantially curved profile extending along longitudinal axis 1a. The additional second portion is complementary to the additional first portion in relation to second working surface 1c and, therefore, totally defined by the additional portions.

First sector 2 and second sector 3 can be made of a single piece.

Radiological filter 1 is designed to remove a component of the x-ray beam and, in particular, the low-energy component. To this end, sectors 2 and 3 are made of a material designed to be passed through, in one embodiment partially, by the x-ray beam. Said material can be aluminum or copper or polymeric materials, such as Teflon.

Emitter 10 comprises at least one radiological filter 1 and, more specifically, only one radiological filter 1. Emitter 10 comprises at least one source 11, in one embodiment one source only, designed to emit a beam of x-rays 10a hitting filter 1 on the surface that is hit. Source 11 is designed to emit an x-ray beam 10a defining a focal spot 11a. It should be noted that radiological filter 1 preferably always remains stationary at focal spot 11a. Source 11 may be of a known type. The radiological filter is between source 11 and patient 1d.

X-ray emitter 10 can comprise a collimator 12 of x-ray beam 10a. Collimator 12 is designed to define the shape of beam 10a hitting radiological filter 1 and then patient 1d. It is located between source 11 and radiological filter 1 so as to intercept the beam before it reaches radiological filter 1. Alternatively, radiological filter 1 is located between source 11 and collimator 12 so as to intercept the beam before it reaches collimator 12.

Radiological filter 1 defines several working conditions based on the portion of first working surface 1b hit by x-ray beam 10a. More specifically, it defines a first operating condition wherein x-ray beam 10a hits, preferably exclusively, first portion 2a, and a second operating condition wherein beam 10a hits at least second portion 3a. In particular, in this condition, X-ray beam 10a exclusively hits second portion 3a or, preferably, second portion 3a and part (more specifically, only a limited part) of first portion 2a. In order to change the operating condition, emitter 10 comprises a handler defining relative motion between radiological filter 1 and x-ray beam 10a and, in particular, between radiological filter 1 and at least one of either collimator 12 or source 11.

Figure 2A:
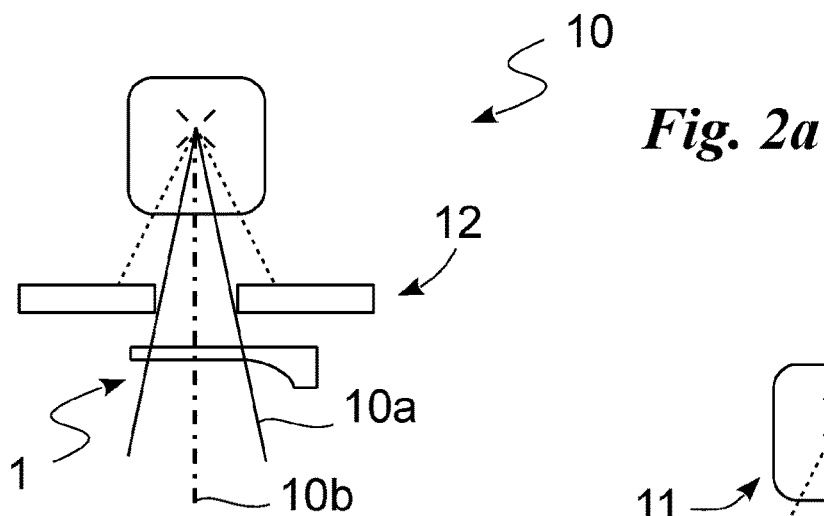
FIGS. 2a-2d show possible configurations of an x-ray emitter comprising the radiological filter according to an embodiment of the present invention.
Figure 2B:
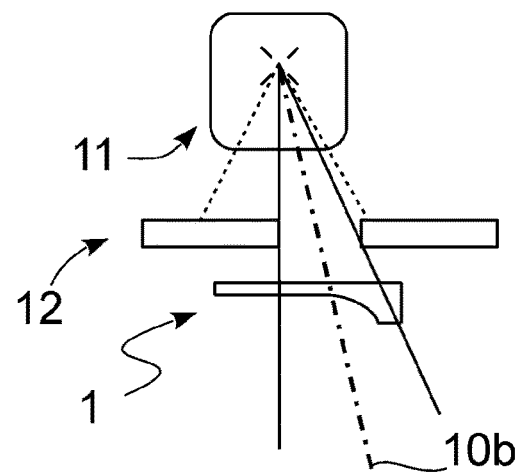
Figure 2C:
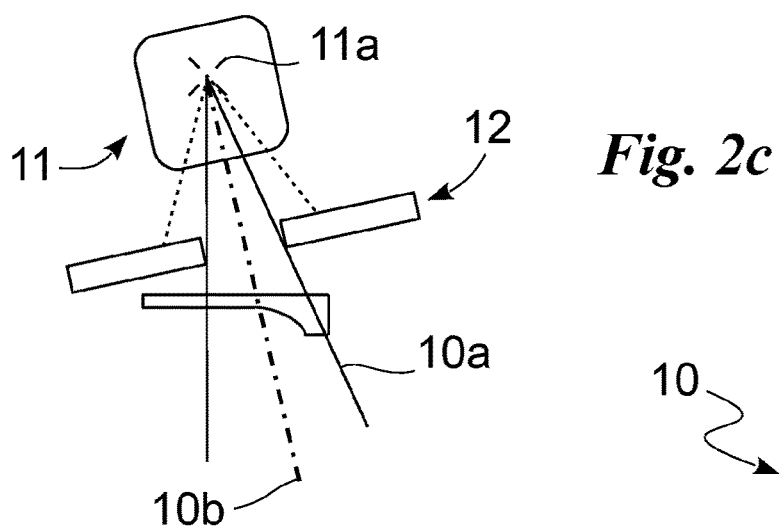
Figure 2D:
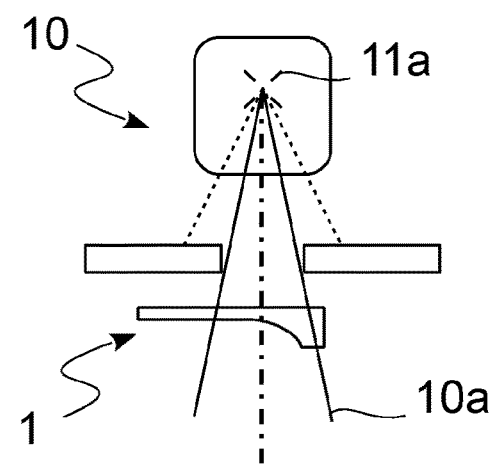

It should be specified that the handler never commands a change of operating condition during scanning. As a result, during the scan, the part of first working surface 1b that x-ray beam 10a hits does not change. The handler can be translational, i.e., designed to change the operating condition of radiological filter 1 by means of a translation along a sliding axis. It can be designed to translate radiological filter 1 in relation to source 11 and, more specifically, to collimator 12 (FIG. 2a and FIG. 2b) or radiological filter 1 and collimator 12 in relation to source 11 (FIG. 2a and FIG. 2d). The sliding axis can be substantially transverse to emission axis 10b. The sliding axis can be substantially transverse and preferably perpendicular to longitudinal axis 1a and, suitably, substantially parallel to second working surface 1b.

Alternatively, the handler can be rotational, i.e., it can be designed to change the operating condition of radiological filter 1 by rotating around a rotation axis. It can be designed to rotate source 11 and, more specifically, collimator 12 in relation to radiological filter 1 (FIG. 2a and FIG. 2c). The rotation axis can be substantially transverse to emission axis 10b. The rotation axis can be substantially parallel to longitudinal axis 1a and, in one embodiment, to second working surface 1b. The rotation axis can pass through focal spot 11a. In some cases, the handler can be both rotational and translational.

Emitter 10 may, additionally, comprise at least one additional radiological filter and an exchange system, such as a slide, for the filter that is hit by the x-ray beam that is designed to enable only one of either radiological filter 1 or the additional filter to be hit by beam 10a. The additional radiological filter may be of a known type.

Radiological imaging device 100 comprises at least one radiological filter 1, in particular at least one emitter 10, suitably of an x-ray beam 10a. In one embodiment radiological imaging device 100 comprises only one emitter 10. In another embodiment, radiological imaging device 100 comprises only one radiological filter 1 so that the x-ray beam passes through only one radiological filter 1. Radiological imaging device 100 comprises at least one detector 20 designed to be hit by x-ray beam 10a after it has passed through filter 1 and at least one sector of the part of patient 1d.

Figure 3A:
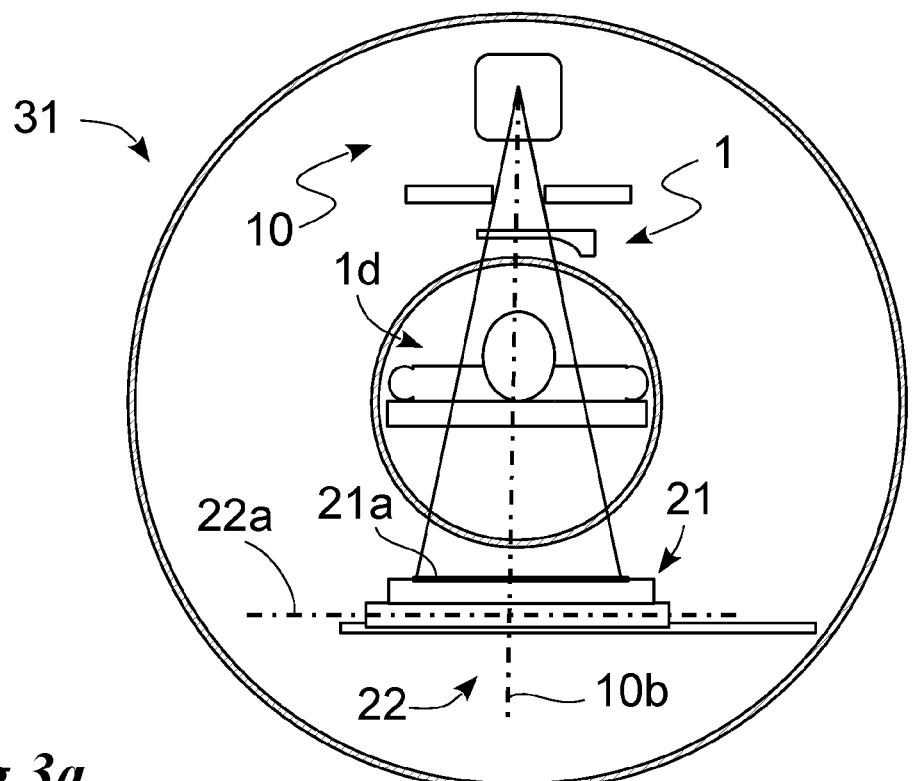
FIGS. 3a-3b present, to scale, a section of an assembly in different configurations of a radiological imaging device equipped with a radiological filter according to an embodiment of the present invention.
Figure 3B:
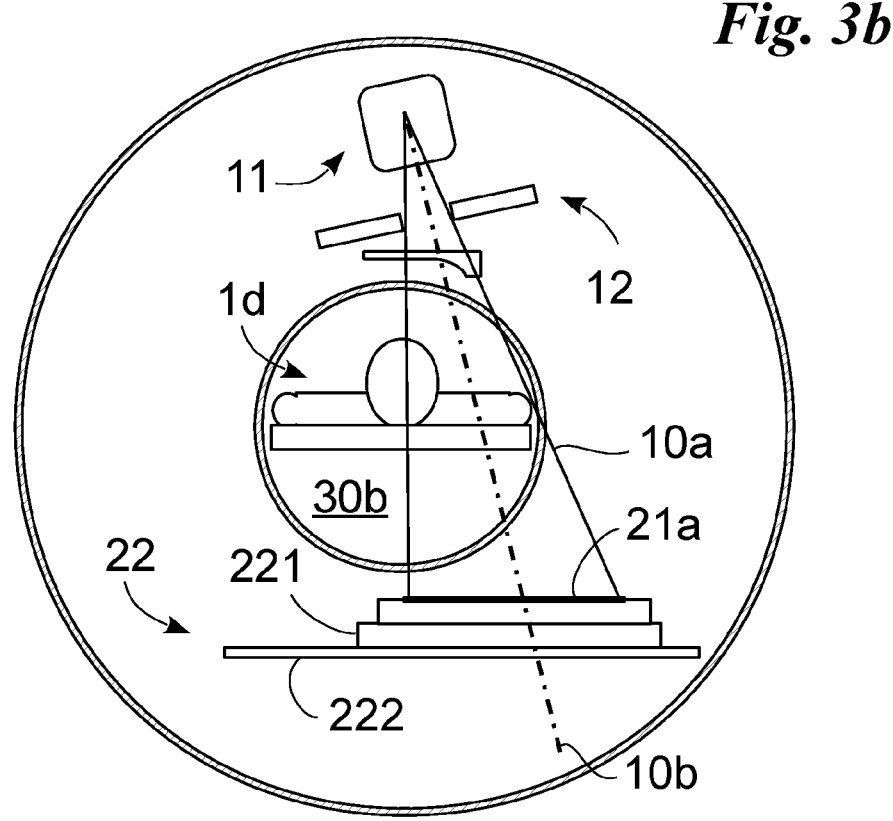

Detector 20 is suitably designed to selectively carry out tomographies, fluoroscopies, and/or radiographies, according to a command given by the operator. Detector 20 comprises at least one sensor 21 defining an x-ray sensitive surface 21a designed to be hit by x-ray beam 10a. Sensitive surface 21a is substantially parallel to longitudinal axis 1a. Detector 20 can comprise a shifting assembly 22 designed to handle sensor 21 in relation to emitter 10 by defining two or more acquisition positions and, in particular, between a first acquisition position (FIG. 3a) and a second acquisition position (FIG. 3b). In the acquisition positions, emission axis 10b can hit the centre of sensitive surface 21a.

Shifting assembly 22 defines a shifting axis 22a and, in one embodiment, a shifting range, i.e., a distance between sensor 21 in the first acquisition position and sensor 21 in the second acquisition position. Preferably, said shifting range is less than the extension of sensitive surface 21a along the shifting axis. As a result, there is an overlap between sensitive surface 21a in the first acquisition position and sensitive surface 21a in the second acquisition position. Shifting axis 22a is substantially parallel to sensitive surface 21a. It is substantially perpendicular to longitudinal axis 1a.

Shifting assembly 22 comprises a cursor 221 connected to sensor 21, a shifting guide 222 defining shifting axis 22a and a motor, more specifically an electric motor, to command the motion of cursor 221 on shifting guide 222.

Radiological imaging device 100 defines multiple working configurations depending on the operating condition and acquisition position. Preferably, it defines a first working configuration, wherein radiological filter 1 is in the first operating condition and sensor 21 is in the first acquisition position (FIG. 3a), and a second working configuration wherein radiological filter 1 is in the second operating condition and sensor 21 in the second acquisition position (FIG. 3b).

Radiological imaging device 100 comprises an anchor block 30 for detector 20 and emitter 10. Anchor block 30 defines an analysis zone 30a between detector 20 and emitter 10 and wherein, suitably, at least one sector of the part of patient 1d is arranged to be scanned.

Radiological imaging device 100 is designed to carry out a scan by carrying out a plurality of acquisitions from different points. Therefore, anchor block 30 is designed to define a motion relative to patient 1d and to the assembly consisting of emitter 10 and detector 20, by defining an acquisition axis 30b. Acquisition axis 30b can be substantially barycentric to analysis zone 30a. It may be substantially parallel to sensitive surface 22a. Acquisition axis 30b can be substantially parallel to longitudinal axis 1a. It should be noted that radiological filter 1 preferably always remains stationary at acquisition axis 30b.

Figure 4:
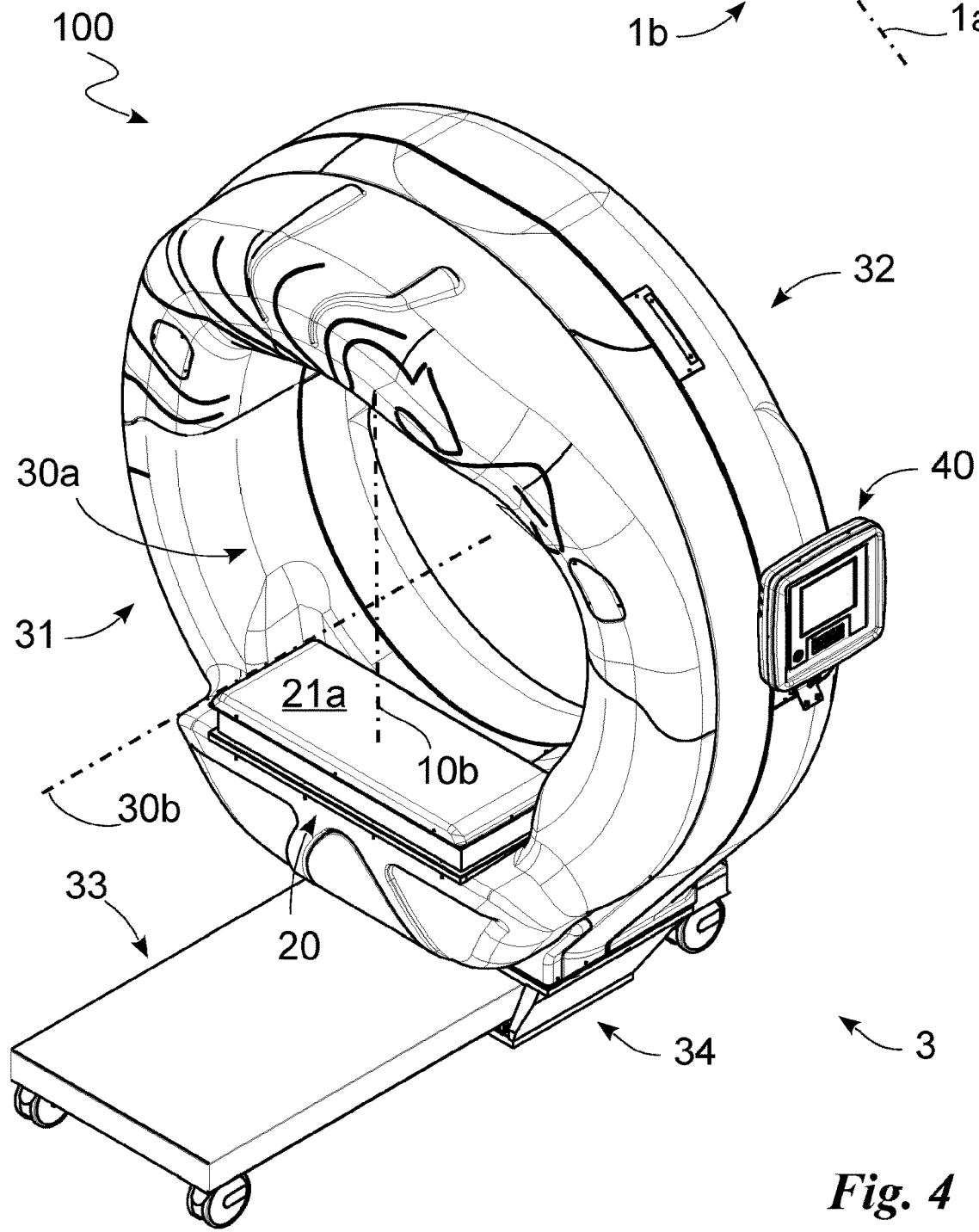
FIG. 4 shows, in scale, a possible radiological imaging device according to an embodiment of the present invention.

Anchor block 30 can be designed to define a reciprocal rotation between patient 1d and the assembly consisting of emitter 10 and detector 20 around acquisition axis 30b and, to be precise, to rotate the emitter-detector assembly in relation to patient 1d around acquisition axis 30b. For this purpose, it comprises a rotor part 31 designed to support emitter 10 and source 20, and a stator part 32 designed to support rotor part 31 allowing it to rotate around acquisition axis 30b. Anchor block 30 may comprise a gantry or C-arm. As an alternative or in addition, anchor block 30 can be designed to define a reciprocal translation between patient 1d and the assembly consisting of emitter 10 and detector 20 along acquisition axis 30b. Acquisition block 30 can, therefore, comprise a track 33 defining the acquisition axis 30b and a carriage 34 to which emitter 10 and detector 20 are connected and designed to run along track 34. Suitably, anchor block 30 is designed to define a reciprocal rotation and translation between emitter assembly 10 and detector 20 and patient 1d. It therefore comprises said rotor part 31, said stator part 32, said track 33, and said carriage 34 to which said parts 31 and 32 are connected as shown in FIG. 4.

Radiological imaging device 100 comprises at least one support for patient 1d. The support is, for example, a radiographic couch.

Radiological imaging device 100 comprises a control unit 40 designed to command the operation of radiological imaging device 100. Control unit 40 is designed to command radiological imaging device 100 with a scan during which the operating condition of radiological filter 1 does not change and, in particular, the working configuration of radiological imaging device 100 does not change. In particular, unit 40 can command a scan carried out with radiological filter 1 in the first operating condition and, in particular, radiological imaging device 100 in the first working configuration, and/or a scan carried out with radiological filter 1 in the second operating condition and, in particular, radiological imaging device 100 in the second working configuration. Control unit 40 may comprise input means (such as a keyboard) designed to enable an operator to command the operation of device 100. It may comprise output means (such as a screen) designed to enable an operator to monitor the operation of device 100 and, in particular, to view acquisitions. Control unit 40 can be connected, in one embodiment so that it can be disconnected, to anchor block 30 and, more specifically, to stator part 31.

Radiological imaging device 100 comprises a support structure for anchor block 30. Radiological imaging device 100 can be mobile and, therefore, the support structure can comprise wheels or other similar elements designed to enable the entire radiological imaging device 100 to move along a walking surface.

The size of radiological filter 1 is defined in relation to emitter 10 and detector 20. The length of first sector 2 and, to be precise, of first portion 2a depends on the position of focal spot 11a and on sensitive surface 21a and on the size of sensitive surface 21a. In detail, the length of first portion 2a (LF1) depends on the distance between focal spot 11a and first portion 2a (DFF), the distance between focal spot 11a and sensitive surface 21a (DFP), and the length of sensitive surface 21a (LS). More specifically, the length of first portion 2a LF1 is defined by the following ratio:

$$DFF:DFP=LF1:LS$$

The length of second sector 3 and, to be precise, of second portion 3a depends on the position of focal spot 11a and of sensitive surface 21a and on shifting assembly 22. More specifically, the length of second portion 3a LF2 depends on DFF, DFP, on the shifting range AP and, in some embodiments, on LS and/or LF1. More specifically, the length of second portion 3a LF2 is defined by the following ratio:

$$DFF:DFP=(1/2*LF1+LF2):(1/2*LS+AP)$$

It should be noted that in this document the term "distance" (such as DFF, DFP) identifies extensions calculated substantially along emission axis 10b; the term "length" (such as LF1, LF2, LS) identifies extensions calculated substantially in the direction perpendicular to emission axis 10b and to longitudinal axis 1a; and the term "range" (such as AP) identifies extensions calculated substantially along shifting axis 22a.

The operation of radiological filter 1, emitter 10, and, in particular, of radiological device 100, described above in structural terms, is as follows. This operation defines an innovative radiological imaging procedure. The radiological imaging procedure comprises a preparation step wherein the part to be analysed is located inside analysis zone 30a. The radiological imaging procedure may comprise a set-up step wherein the scan parameters are set and at least one acquisition step wherein the scan is carried out. In the set-up step, data relating to the part of patient 1d to be analysed and, in particular, at least the length of the patient 1d to be analysed are entered. The measurement of said length may be a direct measurement or may be indirectly derived from other parameters, such as height or weight.

The acquisition step comprises an evaluation sub-step wherein the control unit 40 determines the number of scans and at least one scan sub-step wherein one of said scans is carried out. More specifically, the acquisition step comprises a scanning sub-step for each scan defined in the evaluation sub-step.

In the scanning sub-step, there is no change in the operating condition of the radiological filter, thus leaving the part of the first working surface 1b, which x-ray beam 10a hits, unchanged during scanning. In particular, in the sub-step there is no change in said working configuration of radiological imaging device 100.

By comparing the extension of sensitive surface 21a with the measurements of the part of patient 1d to be analysed, control unit 40 determines the number of scans required.

If the length of sensitive surface 21a is at least equal to the length of the part of patient 1d to be analysed, control unit 40 commands a single scan and then a single scanning sub-step. If the length of sensitive surface 21a is less than the length of the part of patient 1d to be analysed, control unit 40 commands multiple scans and then a scanning sub-step for each of said scans. The number of scans is proportional to the length of sensitive surface 21a and, in particular, to the length of sensitive surface 21a less a safety margin guaranteeing that the images overlap.

In the evaluation sub-step, control unit 40 determines the number of scans and, for each scan, whether radiological imaging device 100 works according to the first working configuration or according to the second working configuration. After determining the number of scans, control unit 40 defines, for each scan, the working condition of radiological imaging device 100 and, in particular, whether it works according to the first or second working configuration. This choice can be made according to at least one type of radiological imaging and the part of patient 1d being scanned (whether a central or lateral part of the torso, etc.).

Usually, in the evaluation sub-step, control unit 40 requires only one scan according to one of the working configurations. Alternatively, control unit 40 requires two scans, one according to the first working configuration and one according to the second working configuration.

In the case of scans with different radiological imaging device 100 working configurations, the acquisition step comprises a configuration change sub-step between adjacent scanning sub-steps with different radiological imaging device 100 working configurations. During the configuration change sub-step, the handler defines relative motion between radiological filter 1 and at least one of either collimator 12 source 11, by enabling a change of operating condition. In addition, in this sub-step, shifting assembly 22 handles sensor 21 by changing its acquisition position.

At the end of the acquisition step, the radiological imaging procedure comprises an analysis step of one or more scans. In the analysis step, control unit 40 processes what has been acquired in one or more scanning sub-steps to obtain the desired radiological image.

Radiological filter 1, emitter 10 and, in particular, radiological device 100 according to the invention achieve important advantages. In fact, radiological filter 1, thanks to the subdivision of the first working surface into two different portions 2a and 3a, enables the filter to carry out acquisitions working either only as a flat filter or as a half bowtie filter combining the peculiarities of a flat filter and a bowtie filter. As a result, radiological filter 1 gives emitter 10 and, in particular, radiological imaging device 100 an advantageous flexibility without increasing their size, construction complexity, or production costs.

This aspect is further enhanced by the presence of sensor 21 with different acquisition positions that makes it possible to define a radiological imaging device 100 characterised by a plurality of working configurations that can be selected according to requirements. This advantage is maximised by the possibility of carrying out radiological imaging using different working configurations, each of which is optimal for the portion under examination. For example, it is possible to carry out radiological imaging, for example a radiography using first portion 2a (i.e., the first operating condition) for the central zone of patient 1d and a tomography using second portion 3a (i.e., the second operating condition) for the outer portion (i.e., near the skin) of patient 1d.

The invention is subject to variations falling within the scope of the inventive concept defined by the claims. In this context, all the elements may be replaced with equivalent elements and the materials, shapes, and dimensions may be as desired.

The invention claimed is:

1. An emitter comprising:
   at least one radiological filter; comprising:
   a first working surface; and
   a second working surface placed opposite the first working surface to enable an x-ray beam to pass through the filter via the first and second working surfaces,
   wherein the first working surface comprises first and second sectors, the first sector defining a first portion, which is substantially flat, and the second sector defining a second portion, which is substantially curved and complementary to the first portion;
   a source configured to rotate about a rotation axis of the source and to emit the x-ray beam hitting the first working surface; and
   a handler defining relative motion between the radiological filter and the x-ray beam by rotating the source about the rotation axis of the source, thereby defining a first operating condition wherein the x-ray beam hits the first portion and a second operating condition wherein the x-ray beam hits at least the second portion.

2. A radiological imaging device comprising:
   the emitter of claim 1; and
   a detector comprising:
   at least one sensor including a surface sensitive to x-rays; and
   a shifting assembly configured to translate the sensor along an axis,
   thereby defining a first acquisition position and a second acquisition position.

3. The radiological imaging device of claim 2, comprising only one radiological filter.

4. The radiological imaging device of claim 3, comprising a first working configuration wherein the radiological filter is in the first operating condition and the sensor is in the first acquisition position and a second working configuration wherein the radiological filter is in the second operating condition and the sensor is in the second acquisition position.

5. The radiological imaging device of claim 4, further comprising an anchor block comprising the detector and the emitter and defining an acquisition axis, wherein:
   the source comprises a focal spot; and
   the position of the acquisition axis and the focal spot does not change between the first working configuration and the second working configuration.

6. The radiological imaging device of claim 2, wherein:
   the source comprises a focal spot; and
   the length of the first portion is based on the distance between the focal spot and the first portion, the distance between the focal spot and the sensitive surface, and the length of the sensitive surface.

7. A radiological imaging procedure implemented by the radiological imaging device of claim 2, comprising an acquisition step comprising at least one scanning sub-step, wherein there is no change in the working configuration of the radiological imaging device during the scanning sub-step.

8. A radiological imaging procedure implemented by the radiological imaging device of claim 2, comprising an acquisition step comprising a plurality of scanning sub-steps at least partly carried out with a different said working configuration of the radiological imaging device, wherein the acquisition step comprises a configuration change sub-step between adjacent scanning sub-steps in different working configurations of the radiological imaging device.

9. The radiological imaging device of claim 2, comprising a first working configuration wherein the radiological filter is in the first operating condition and the sensor is in the first acquisition position and a second working configuration wherein the radiological filter is in the second operating condition and the sensor is in the second acquisition position.

10. The radiological imaging device of claim 9, further comprising an anchor block comprising the detector and the emitter and defining an acquisition axis, wherein:

the source comprises a focal spot; and the position of the acquisition axis and the focal spot does not change between the first working configuration and the second working configuration.

11. The radiological imaging device of claim 10, further comprising a control unit configured to command a scan of a patient that is performed by keeping the radiological imaging device in one of the first or second working configurations.

12. The radiological imaging device of claim 10, wherein:

the shifting assembly defines a shifting range; and the length of the second portion is based on the distance between the focal spot and the first portion, the distance between the focal spot and the sensitive surface, the length of the sensitive surface, and on the shifting range.

13. The radiological imaging device of claim 9, further comprising a control unit configured to command a scan of a patient that is performed by keeping the radiological imaging device in one of the first or second working configurations.

14. The emitter of claim 1, wherein the rotation axis of the source passes through a focal spot of the source.

* * * * *